US006406701B1

(12) United States Patent
Pulido-Cejudo (10) Patent No.: US 6,406,701 B1
(45) Date of Patent: Jun. 18, 2002

(54) METHOD AND COMPOSITIONS FOR PREVENTING OR REDUCING HIV INFECTION

(75) Inventor: Gabriel Pulido-Cejudo, Ottawa (CA)

(73) Assignees: Canbreal Therodiagnostics Canada Holding Corporation (CA); Her Majesty the Queen in right of Canada as represented by the Minister of Health (CA)

( * ) Notice: Subject to any disclaimer, the term of this patent is extended or adjusted under 35 U.S.C. 154(b) by 0 days.

(21) Appl. No.: 09/538,827

(22) Filed: Mar. 30, 2000

(30) Foreign Application Priority Data

Mar. 30, 2000 (CA) ............................................. 2267481

(51) Int. Cl.$^7$ ............................................. A61K 39/12
(52) U.S. Cl. ............................... 424/198.1; 435/70.21; 435/24; 530/388.26
(58) Field of Search ............................... 435/70.21, 24; 424/142.1, 146.1, 154.1, 198.1; 514/2; 530/388.26

(56) References Cited

PUBLICATIONS

Chan "L–leucinthiol–a potent inhibitor of leucine aminopeptidase", Biochemical and Biophysical Research Communications, vol. 116, No. 1(Oct. 14, 1983) 116(1) pp. 297–302.*
Frohne "Untersuchungen zum Einfluss von Glutathion auf die katalytischen Eigenschaften der Leuzinaminopeptidase [Influence of glutathione on the catalytic properties of leucine aminopeptidase]" Acta Biologica et Medica Germanica, vol. 35, No. 3–4(1976) 359–64. Abstract only.*
Pulido–Cejudo G. et al: "Plasma Leucine Aminopeptidase In HIV–Infected Patients." VIII International Conference On Aids And The III STD World Congress; Harvard–Amsterdam Conference, Amsterdam, Netherlands, Jul. 19–24, 1992. XP002145325.
Mathe G.: "Bestatin, an aminopeptidase inhibitor with a multi–pharmacological function." Biomedicine and Pharmacotheory, (1991) 45 (2–3) 49–54. XP000916750.
Deng, Jing T. et al: "Purification of Circulating Liver Plasma Membrane Fragments Using A Monoclonal Antileucine Aminopeptidase Antibody", Hepatology (Philadelphia) (1996), 23(3), 445–54, XP000916789.
Mesange F. et al: "Ligands of the Antiestrogen–Binding Site Are Able to Inhibit Virion Production of Human Immunodeficiency Virus 1–Infected Lymphocytes." Molecular Pharmacology, (Jul. 1996) 50 (1) 76–79., XP000916761.

Sen, Chandan K.: "Redox Signaling and the Emerging Therapeutic Potential of Thiol Antioxidants." Biochemical Pharmacology, (Jun. 1, 1998) 55 (11) 1747–1758. Ref: 134, XP000916754.
Pulido–Cejudo, Gabriel et al: "Critical Interdependency: From the Role of Estrogen on Breast Cancer to the Susceptibility of Women Towards HIV Infection", NATO Sci. Ser., Ser. A (1999), 311 (Intermolecular Cross–Talk In Tumor Metastasis), 123–136, XP000916826.
PCT International Search Report; PCT Application No. PCT/CA00/00331; filed Mar. 30, 2000.
Laurence J., Cooke H., Sikder S.K. "Effect of Tamoxifen on Regulation of Viral Replication and Human Immunodeficiency Virus (HIV) Long Terminal Repeat–Directed Transcription in Cells Chronically Infected with HIV–1". Blood Feb. 1, 1990; 75(3):696–703.
Mathe G. "Bestatin, An Aminopeptidase Inhibitor with a Multi–Pharmacological Function". Biomed & Pharmacother 1991; 45(2–3):49–54.
Mesange F., Delarue F., Puel J. Bayard F., Faye J.C. "Ligands of the Antiestrogen–Binding Site Are Able to Inhibit Virion Production of Human Immunodeficiency Virus 1–Infected Lymphocytes". Molecular Pharmacology Jul. 1996; 50(1):75–79.
Pulido–Cejudo, G., Conway, B., Proulx, P., Brown, R., and Izaguirre, C.A. (1997). "Bestatin–Mediated Inhibition of Leucine Aminopeptidase May Hinder HIV Infection". Antiviral Research, 36:167–177.
Pulido–Cejudo Gabriel et al.;"Critical Interdependency: From the Role of Estrogen on Breast Cancer to the Susceptibility of Women Towards HIV Infection."; Intermolecular Cross–Talk in Tumor Metastasis; Series A: Life Sciences–vol. 311; Skouteris George G. and Nicolson Garth L.; IOS Press, 1999; Washington D.C.. pp. 123–136.

* cited by examiner

Primary Examiner—Jeffrey Stucker
(74) Attorney, Agent, or Firm—Thompson Hine LLP (57) ABSTRACT

In spite of having achieved an in depth and comprehensive genetic structure of the human immunodeficiency virus (HIV) and of that of its several structural and geographical clusters, a very limited success in the prevention and treatment of AIDS has been attained. Described herein is a method for preventing or reducing HIV infectivity by using an antibody specific for estrogen-stimulated leucine aminopeptidase (es-LAPase), or one or more inhibitors of LAPase activity, or a combination thereof. Also described is a method for preventing or reducing HIV infectivity by using an antibody specific for es-LAPase, one or more inhibitors of es-LAPase activity and an anti-estrogen compound. The novel compositions are also defined.

35 Claims, 3 Drawing Sheets

METHOD AND COMPOSITIONS FOR PREVENTING OR REDUCING HIV INFECTION

The present invention relates to a method to inhibit HIV infection by using an antibody to estrogen-stimulated leucine aminopeptidase (es-LAPase) or one or more inhibitors of es-LAPase activity, or a combination thereof. The invention further relates to a method to inhibit HIV infection by using an antibody to es-LAPase, one or more inhibitors of es-LAPase activity and an anti-estrogen compound. Novel compositions which inhibit HIV infection are also part of the present invention.

BACKGROUND OF THE INVENTION

In spite of having achieved an in depth and comprehensive genetic structure of the human immunodeficiency virus (HIV) and of that of its several structural and geographical clusters, a very limited success in the prevention and treatment of AIDS has been attained. Although HIV and its variants are well characterized as the prime causative agents leading to the human acquired immunodeficiency syndrome (AIDS), a less comprehensive identification of key cellular factors involved in the early molecular mechanisms leading to viral entry have been accomplished.

CD4 T-cells are the principal target of HIV infection as shown from both in vitro and in vivo studies. The CD4 glycoprotein at the surface of T-cells exhibits a high affinity for HIV virions. Other molecules, particularly from the chemokine-receptor family, also participate to promote viral entry into target cells.

Therapeutics modalities to thwart the progress of the disease in HIV infected patients relies principally on two types of medications: Reverse transcriptase inhibitors and protease inhibitors. Although successful at slowing the replication of the virus, they are limited by the high rate of mutagenesis in the virus which results in modification of the drugs' binding site and their concomitant lost of efficacy. One approach to resolve the problem has been to administer several drugs simultaneously to lower the probability of the development of resistant strains of the virus. However, these multidrug regimen create serious side effects. As a result compliance may be low.

Furthermore, current therapies for HIV infections are not specific for particular groups of individuals such as women. In a recent report it was found that the number of women infected with HIV during 1991 and 1995 increased by 63%, more than any other group of people that had contracted AIDS, regardless of race or mode of exposure to HIV virus [Centers for Disease Control and Prevention. (1996). *HIV/ AIDS Surveill. Rep.* Centers for Disease Control and Prevention; 8. Atlanta, Ga.]. The increased incidence of AIDS epidemic on morbidity and mortality among women (ages of 25–44) has been recently confirmed by other groups [Wortley, P. M., and Flemming, P. L. (1997). AIDS in Women in the United States: Recent Trends. *JAMA,* 278: 911–916.]. The reasons for the increased incidence of AIDS in women are largely unknown. Not only women are more prone to infection than men (supra) but studies have shown that anti-HIV drugs work differently in women and men. For example, toxicities, side effects and blood levels have been shown to be gender specific. Hormonal differences between men and women are cited to explain the differences but no clear link has been established. In view of the above data, there is a need to tailor therapeutic modalities to exploit the differences in the infection process between men and women to improve the efficiency of treatments.

Independently of the role of CD4, the putative receptor for HIV and that of the β-chemokine co-receptors (CKR-5, CCR5 and CXCR-4), we have described the important role of both membrane-bound and extracellular Leucine Aminopeptidase in HIV viral entry. (Pulido-Cejudo, G. et al. (1997) Antiviral Research 36, 167–177).

The present invention overcomes the limitation of the prior art by providing a link between LAPase activity and estrogen. This link has been exploited herein to discover new HIV viral inhibitors which can be used alone or in combination with improved efficacy.

SUMMARY OF THE INVENTION

The present invention relates to a method to inhibit HIV infection by using an antibody to es-LAPase or an inhibitor of es-LAPase activity, or a combination thereof. The invention further relates to a method to inhibit HIV infection by using an antibody to es-LAPase, an inhibitor of es-LAPase activity and an anti-estrogen compound. Novel compositions which inhibit HIV infection are also part of the present invention.

Thus according to the present invention there is provided a method for reducing HIV infectivity towards T lymphocytes comprising contacting said T lymphocytes with a sufficient amount of an inhibitor of LAPase.

In a further embodiment of the present invention there is provided a method for reducing HIV infectivity towards T lymphocytes comprising contacting said T lymphocytes with a sufficient amount of an antibody specific for LAPase, more specifically a monoclonal antibody specific for es-LAPase.

This invention also provides a method for reducing HIV infectivity towards T lymphocytes comprising contacting said T lymphocytes with a sufficient amount of an antibody specific for es-LAPase and an inhibitor of LAPase.

This invention also provides a method for reducing HIV infectivity towards T lymphocytes comprising contacting said T lymphocytes with a sufficient amount of an antibody specific for es-LAPase, an inhibitor of LAPase and an anti-estrogen compound.

Further according to the present invention there is provided a method for preventing or reducing HIV infection comprising administering to a patient in need thereof, a pharmaceutically effective amount of a composition which comprises an antibody specific to es-LAPase and a pharmaceutically acceptable carrier.

Also provided in this invention is a method for preventing or reducing HIV infection comprising administering to a patient in need thereof, a pharmaceutically effective amount of a composition which comprises an inhibitor of LAPase and a pharmaceutically acceptable carrier.

This invention is also directed to a method for preventing or reducing HIV infection comprising administering to a patient in need thereof, a pharmaceutically effective amount of a composition which comprises an antibody specific to es-LAPase and an inhibitor of LAPase together with a pharmaceutically acceptable carrier.

This invention is also directed to a method for preventing or reducing HIV infection comprising administering to a patient in need thereof, a pharmaceutically effective amount of a composition which comprises an antibody specific to es-LAPase, an inhibitor of LAPase and an anti-estrogen compound together with a pharmaceutically acceptable carrier.

Also according to the present invention there is provided a composition comprising an antibody specific to es-LAPase and an inhibitor of LAPase.

Also according to the present invention there is provided a composition comprising an antibody specific to es-LAPase, an inhibitor of LAPase and an anti-estrogen compound.

BRIEF DESCRIPTION OF THE DRAWINGS

These and other features of the invention will become more apparent from the following description in which reference is made to the appended drawings wherein.

DETAILED DESCRIPTION OF PREFERRED EMBODIMENT

The present invention relates to a method to inhibit HIV infection by using an antibody to es-LAPase or an inhibitor of es-LAPase activity, or a combination thereof. The invention further relates to a method to inhibit HIV infection by using an antibody to es-LAPase, an inhibitor of es-LAPase activity and an anti-estrogen compound. Novel compositions which inhibit HIV infection are also part of the present invention.

It has been observed that, independently of the role of CD4, the putative receptor for HIV and that of the β-chemokine co-receptors (CKR-5/CCR5;CXCR-4), both membrane-bound and extracellular leucine aminopeptidase (LAPase;EC 3.4.11.1) can promote HIV entry in T lymphocytes (Pulido-Cejudo et al. Antiviral Res. 36:167–177, 1997).

In the present invention it is disclosed that LAPase activity in T lymphocytes and in breast cancer parental cells can be stimulated by estrogens, or estrogen analogues. One aspect of this invention is directed to the identification and purification of an estrogen-stimulated LAPase isoenzyme, referred to herein as es-LAPase. Details of the estrogen-stimulated LAPase isoenzyme are described in Applicants copending application entitled "A Monoclonal Antibody against Estrogen Stimulated Leucine Aminopeptidase", which is incorporated herein by reference.

A further aspect of the present invention is the preparation of antibodies against the es-LAPase isoenzyme. Antibodies can be produced by methods well known in the art. In general, the antibody producing cells are prepared by immunizing an animal, for example, mouse, rat, rabbit, sheep, horse, or bovine, with an antigen. The immunization schedule and the concentration of the antigen in suspension is such as to provide useful quantities of suitably primed antibody producing cells. These antibody producing cells can be either spleen cells, thymocytes, lymph node cells and/or peripheral blood lymphocytes.

The antibody producing cells are then fused with myeloma cells, cell lines originating from various animals such as mice, rats, rabbits, and humans can be used, using a suitable fusion promoter. Many mouse myeloma cell lines are known and available generally from members of the academic community and various depositories, such as the American Type Culture Collection, Manassas, Va. The myeloma cell line used should preferably be medium sensitive so that unfused myeloma cells will not survive in a selective media, while hybrids will survive. The cell line most commonly used is an 8-azaguanine resistant cell line, which lacks the enzyme hypoxanthine-guanine-phosphoribosyl-transferase and therefore will not be supported by HAT (hypoxanthine-aminopterin-thymidine) medium. In general, the cell line is also preferably a "non-secretor" type, in that it does not produce any antibody. The preferred fusion promoter is polyethyleneglycol having an average molecular weight from about 1000 to about 4000. Other fusion promoters such as polyvinylalcohol, a virus or an electrical field can also be used.

The immortalized cells (hybridoma) must then be screened for those which secrete antibody of the correct specificity. The initial screening is generally carried out using an enzyme-linked immunosorbent assay (ELISA). Specifically, the hybridoma culture supernatants are added to microtitre plates which have been previously coated with the antigen, in this case the es-LAPase. A bound specific antibody from the culture supernatants can be detected using a labelled second antibody, for example, goat antimouse IgG labelled with peroxidase, which is commercially available. Cultures that are positive against the es-LAPase are then subjected to cloning by the limiting dilution method. Secondary hybridoma cultures are re-screened as described above, and further positive cultures are then examined using the BIAcore system (Pharmacia Biosensor AB, Uppsala, Sweden). The cultures are then evaluated as to determine whether or not the antibody binds the antigen and to determine the kinetic profile of antigen binding. Selected cultures based on these results are subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the sub-population exhibits the production of a specific antibody, which is indicative of the "stability" of the hybridoma. In addition, hybridoma culture wells often have multiple colonies some of which may be antibody non-producers. The cloning process allows the selection of a positive hybrid which is derived from a single cell.

In one embodiment of the present invention there is provided a monoclonal antibody, specific against the es-LAPase, which has been designated Mab 7B6. This monoclonal antibody does not inhibit the enzymatic activity of LAPase. For this reason it will be referred to hereinafter as a non-inhibitory monoclonal antibody. A hybridoma cell line producing this monoclonal antibody had been deposited with the International Depositary Authority of Canada, Winnipeg, Manitoba on Mar. 22, 2000, in compliance with the Budapest Treaty.

The present invention also encompasses MAb 7B6 and any fragments thereof containing the active binding region of the antibody such as Fab, F(ab)$_2$ and Fv fragments. These fragments can be obtained from the 7B6 antibody by using techniques well known to those of skills in the art (Rousseaux et al. Methods Enzymology, 121:663–69, Academic Press, 1986).

A further embodiment of the present invention encompasses antibodies or fragments thereof capable of binding the same antigenic determinant as the 7B6 antibody. Including, but not limited to, antibodies possessing the same antigenic specificity as the 7B6 antibody but originating from a different species or having a different isotype or exhibiting different binding affinities. It is envisioned that class and isotype variants of the antibody of the present invention can be prepared using recombinant class switching and fusion techniques that are well known to those skilled in the art (see for example: Thammana et al. Eur. J. Immunol, 13:614, 1983; Oi et al., Biotechnologies, 4(3):214–221, Liu et al. Proc. Nat. Acad. Sci. (USA), 84:3439–43, 1987; Neuberger et al., Nature 312:604–608, 1984 and Spira et al. J. Immunol. Meth., 74:307–15, 1984).

The monoclonal antibody of the present invention can be produced either using a bioreactor or from ascites, both procedures of which are well known in the art.

In one embodiment of the present invention there is provided a method of reducing HIV infection wherein Mab 7B6 is incubated with T lymphocytes prior to and during infection with HIV-1. This incubation prevents or reduces the infectivity of HIV-1 towards T lymphocytes. Even though not described in the examples (infra), this embodiment also encompasses incubating T lymphocytes with Mab 7B6 after they have been infected with HIV-1 to reduce further infection as would be obvious to one skilled in the art.

The monoclonal antibody can be added directly to the incubation medium or it can be coupled to a solid matrix. The solid matrix can be any matrix, as would be known to someone skilled in the art, onto which the antibody can be coupled as long as this coupling does not interfere with the binding of the antibody to its epitope on es-LAPase. The solid matrix can be, but is not limited to, a protein G matrix. Without wishing to be bound by any theory, the coupling of the antibody to the matrix may reduce the level of non-specific binding of the anti-body to its epitope.

HIV infection of T lymphocytes can be measured using a number of techniques. The three most commonly used are the quantification of viral capsid protein p24 production, cyopathycity, and the determination of proviral load by polymerase chain reaction (PCR)(Conway et al., Clin. Diag. Virol. 3:95–104, 1995). These methods are well known in the art. Other methods as would be known to one skilled in the art may also be used to determine the levels of HIV infectivity.

According to one aspect of the present invention anti-es-LAPase antibodies are used to reduce HIV infection. According to this embodiment of the present invention cells can be treated at a concentration of from about 50 ng to about 200 ng of antibody per 10 ml of cells, wherein the cells are at a density of about $1.0 \times 10^5$ cells/ml. The preferred amount of antibody can be determined empirically, by a person of ordinary skill in the art. In one example of this embodiment the concentration of antibody used is about 100 ng per 10 ml of cells.

The present invention also discloses that thiol containing compounds unexpectedly inhibit the activity of es-LAPase. By thiol containing compounds it is meant any compound having a SH group such as, but not limited to, peptides having reduced cysteine residues. In one embodiment of this aspect of the invention, thioredoxin and glutathione have been found to inhibit es-LAPase.

Thus, in a further embodiment of the present invention, there is provided a method wherein an inhibitor of es-LAPase is incubated with T lymphocytes prior to and during infection with HIV. According to this aspect of the invention, the inhibitor of es-LAPase activity can be a competitive, an uncompetitive or non-competitive inhibitor. The meaning of these terms is taken in the context of the enzyme kinetic theory, as would be known to persons skilled in the art. In this aspect of the invention, an example of an uncompetitive inhibitor is thioredoxin and an example of a non-competitive inhibitor is glutathione.

The inhibitor of LAPase can be added directly to the incubation medium or it can be coupled to a solid matrix. The solid matrix can be any matrix, as would be known to someone skilled in the art, onto which the inhibitor can be coupled as long as this coupling does not interfere with the binding of the inhibitor to es-LAPase. The solid matrix can be, but is not limited to, DPDP, an amide bonding matrix (Pierce, Rockford, Ill. USA).

In this aspect of the present invention the inhibitors of es-LAPase activity are used to reduce HIV infection. According to this embodiment of the present invention cells can be treated with the inhibitor at a concentration of from about $10^{-8}$M to about $10^{-5}$M, wherein the cells are at a density of about $1.0 \times 10^5$ cells/ml. The preferred amount of inhibitor can be determined empirically, by a person of ordinary skill in the art. In one example of this embodiment the concentration of inhibitor used is from about 4 ng to about 8 ng per ml of cells.

In another aspect of the present invention there is provided a method wherein an antibody to es-LAPase and an inhibitor of LAPase can be combined and incubated with T lymphocytes prior, during or after infection with HIV to reduce HIV infectivity. In this aspect of the present invention, the antibody and inhibitor are used together according to the methods already disclosed for their individual use.

In a previous publication (Mesange et al. Mol. Pharmacol., 50:75–79, 1996) it has been shown that Tamoxifen, an anti-estrogen compound can reduce HIV infectivity. However, incomplete inhibition of HIV infection were observed at Tamoxifen concentrations of $10^{-6}$M or higher. In a further aspect of the present invention there is provided a method wherein not only Tamoxifen but other anti-estrogens can be used together with an antibody to es-LAPase and an inhibitor of LAPase to reduce HIV infectivity.

In this example of the present invention the anti-estrogen compound is selected from the following, used alone or in combination: 4-hydroxyandrostenedione, Raloxifene, 3β,5α-tetrahydro Norethisterone, Tamoxifen, Droloxifene and Idoxifene. In this aspect of the present invention the anti-estrogen compound is used at a final concentration ranging from about $10^{-6}$ M to about $10^{-8}$ M. The concentrations of the other components in this method are used as describe above.

In a further aspect of this invention a competitive inhibitor of es-LAPase activity can also be used together with the above described compounds. An example of a suitable competitive inhibitor is Bestatin, but the invention also encompasses other competitive inhibitors such as Amastatin.

The present invention also encompasses a method for treating patients infected with HIV, or at risk of being infected, with an antibody to es-LAPase or one or more inhibitors of es-LAPase activity or a combination thereof. The present invention also encompasses a method for treating patients infected with HIV, or at risk of being infected, with an antibody to es-LAPase, one or more inhibitors of es-LAPase activity and an anti-estrogen. In this aspect of the invention there is provided a pharmaceutical composition comprising an antibody to es-LAPase. In a further aspect of this embodiment the pharmaceutical composition comprises one or more inhibitors of es-LAPase activity. In a still further aspect of this embodiment the pharmaceutical composition comprises an antibody to es-LAPase and one or more inhibitors of es-LAPase activity. In a still further aspect of this embodiment the pharmaceutical composition comprises an antibody to es-LAPase and one or more inhibitors of es-LAPase activity and an anti-estrogen compound.

Pharmaceutical compositions of the present invention generally will include a therapeutically effective amount of at least one of the compounds referred to above together with a pharmaceutically effective carrier. The antibody of the present invention may be administered by any means that enables the active agent to reach the agent's site of action in the body of a mammal. In the case of the antibodies of this invention, the primary focus is the ability to reach and bind with both membrane-bound and extra cellular es-LAPase. Because proteins are subject to being digested when administered orally, parenteral administration, i.e., intravenous, subcutaneous, intramuscular, would ordinarily be used to optimize absorption.

The antibodies of this invention may be administered either as individual therapeutic agents or in combination with other therapeutic agents, as discussed above. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95% by weight based on the total weight of the composition.

For parenteral administration, the antibody can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

In further embodiments of the present invention, the antibody can be administered together with one or more LAPase inhibitors, as discussed in detail above. In this embodiment, the LAPase inhibitors can be added at a dose of about 0.1 to about 100 milligrams per kilogram of body weight.

In yet a further embodiment of the present invention, the antibody can be administered together with one or more anti-estrogen compound, as discussed in detail above. In this embodiment, the anti-estrogen compound can be added at a dose of about 0.1 to about 100 milligrams per kilogram of body weight.

In another embodiment of the present invention, the antibody can be administered together with one or more LAPase inhibitors and one or more anti-estrogen compounds as discussed in detail above. In this embodiment, both the LAPase inhibitors and anti-estrogen compounds can be added at doses of about 0.1 to about 100 milligrams per kilogram of body weight.

The antibody and the inhibitors to be included in the pharmaceutical composition may be coupled to a matrix as described above, as long as the matrix is non-toxic to mammals. Coupling of the antibody and the inhibitors to an appropriate matrix may also facilitate the incorporation of these compounds into liposomes.

In a further embodiment, the inhibitor of LAPase in the pharmaceutical composition is the uncompetitive inhibitor thioredoxin, which may be maintained in its reduced state by including reducing compounds in the composition. Such compounds may include but are limited to glutathione and cysteine.

In order that the invention described herein may be more fully understood, the following examples are set forth. It should be understood that these examples are for illustrative purposes only and are not to be construed as limiting the scope of this invention in any manner.

EXAMPLES

Example 1

Estrogen Mediated LAPase Release from HUT78 Cells

CD4$^+$ T-HUT78 cells were incubated in the presence of various concentrations of 17-β-Estradiol and LAPase levels were determined as described by G. Pulido-Cejudo et al. (Antiviral Research, 36:167–177, 1997).

Table 1 show that estrogen promoted the release of LAPase in HUT78 cells in a dose response manner, with a maximum stimulation observed at $10^{-7}$M.

TABLE 1

| Extracellular LAPase activity of HUT78 cells incubated with 17-β-Estradiol | | |
|---|---|---|
| [β-Estradiol] | Control | LAPase activity (U* × $10^{-5}$/ml) 17-β-Estradiol Stimulation |
| $10^{-5}$ M | 4.2 | 10.8 |
| $10^{-6}$ M | 5.6 | 20.4 |
| $10^{-7}$ M | 4.8 | 148.6 |
| $10^{-8}$ M | 5.7 | 110.7 |

*One unit of LAPase is defined as the amount of enzyme required to hydrolyze 1 μmol of L-leucine-β-naphthylamide to L-leucine and β-naphthylamide per min at pH 7.5 and 37° C.

Figure 1:
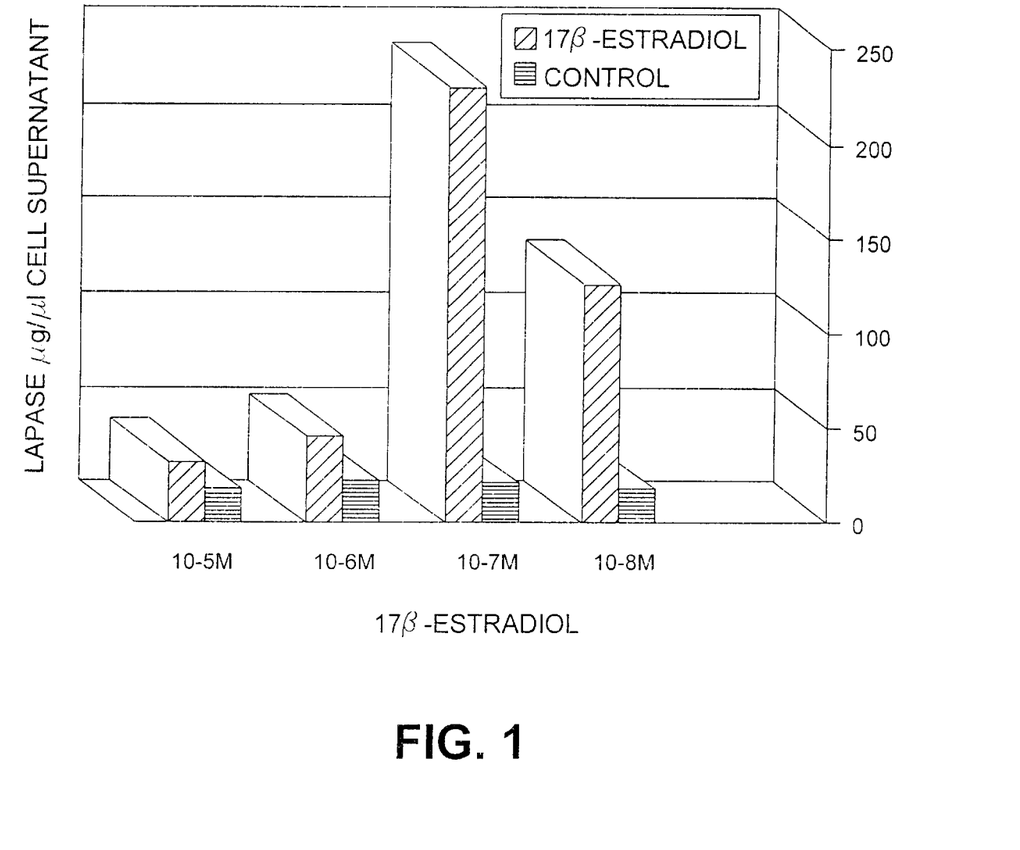
FIG. 1 shows the effect of estrogen on LAPase activity in cell supernatents of primary parental breast cancer cell lines.

Following estrogen stimulation, maximum release of LAPase from breast carcinoma parental cells was observed at an estrogen (17β-Estradiol) concentration of 100 nM following 24 hours of incubation (see FIG. 1 where LAPase activity was determined in supernatants of primary parental cell lines immunoprecipitated with anti-LAPase-Sepharose bound MAb 7B6 antibodies. Cells were incubated in the presence of 17-β-Estradiol and following a 24 hr incubation, supernatants were removed from the primary culture, immunoprecipitated and assayed fluorometrically for LAPase activity by the method of Kuramochi et al. [1987, *J. Antibiot.*, 40: 1605:1611] Control cells were cultured in the absence of 17-β-Estradiol.). During the same period, LAPase in cell supernatants of control cells remain unchanged. In addition, LAPase activity was determined in supernatants of primary parental cell lines immunoprecipitated with anti-LAP-Protein G MAb 7B6 bound antibodies.

These results show that the extracellular LAPase activity of estrogen stimulated cells (100 nM) was $7.7\times10^{-5}$ U/ml in comparison to $6.4\times10^{-6}$ U/ml detected in the supernatant of parental cells incubated for 24 hours with cell media alone as control. In addition, there was no effect of estrogen incubation on LAPase activity in purified preparations of this enzyme alone. Collectively, these results suggest that estrogen effect on LAPase activity encompasses a cellular mediated process.

Example 2

Purification of es-LAPase

Primary parental breast carcinoma cells obtained from human tumour biopsies were stimulated with 100 nM 17-β-Estradiol for 24 hours or cell media alone as a control. The cell media was RPMI 1640 medium+10% FCS+100 U/ml Penicillin+100 μg/ml Streptomycin. Cell supernatants were collected and then dialyzed against PBS in seamless cellulose tubing (MW 12,400) for 12 hours at 4° C. Es-LAPase was subsequently purified from the dialyzed cell supernatants using HPLC-gel permeation followed by DEAE-Cellulose and Bestatin-Sepharose affinity Chromatography. Briefly, the cell supernatant was applied to a Bio-Sil SEC-250 column (600×7.5 mm) previously equilibrated in a buffer containing 100 mM Sodium Phosphate buffer pH 6.8, 100 mM $Na_2SO_4$, 1 μM $ZnCl_2$ and 10% glycerol. The column was washed with 300 ml of the same buffer at a flow rate of 0.5 ml/min. Protein was concentrated to 10 ml by ultrafiltration using YM5 membrane (5000 M.W. cutoff, Amicon Div., Danvers, Mass., USA). The concentrate was applied to a DEAE cellulose column (2.6 cm×28.5 cm) equilibrated and washed with 50 mM Tris-HCl buffer pH 7.5; 1 μM $ZnCl_2$; and 10% (v/v) glycerol. Es-LAP was eluted using a linear gradient (0 to 1M NaCl in Tris buffer) at a flow rate of 0.50 ml/min. A Bestatin-affinity column was prepared using Ultralink. EDC/DADPA Amide bonding matrix (Pierce, Rockford, Ill. U.S.A.) by reacting 100 mg of pure Bestatin with the carbodiimide EDC/DADPA matrix following the procedure provided by the manufacturer. Prior to loading the LAPase containing eluent, the Bestatin-affinity column was equilibrated with 10 mM Tris-HCl pH 8.0 containing 1 μM $ZnCl_2$ and washed with 300 ml of this binding buffer. Es-LAPase was recirculated through the system using a peristaltic pump at a flow rate of 0.10 ml/min, for 2 hours. Following this recirculation, the column was washed with eight column volumes of binding buffer.

Bestatin-bound es-LAPase was eluted with a linear gradient (0–0.5 M NaCl) prepared in binding buffer 10 mM Tris-HCl pH 8.0 containing 1 μM $ZnCl_2$. Elution of bound es-LAPase was monitored by absorbance at 280 nm. Purified es-LAPase fractions were aliquoted in 500 μl and stored until further use in 50 mM Tris-HCl pH 7.8 and 50 μM $ZnCl_2$. Es-LAPase Protein concentration was estimated by the method of Lowry et al. [J Biol Chem 193:265 (1951)] using bovine serum albumin as a standard. A summary of the purification fold of the 17-β-Estradiol-stimulated LAPase from parental cells of human breast carcinomas is set out in Table 2. Es-LAPase was purified to an approximate 7000 fold after the last Bestatin-affinity chromatographic step.

Es-LAPase activities were determined fluorometrically using leucine-b-naphthylamide as the substrate [Kuramochi, H., et al. (1987) J. Antibiot., 40,1605–1611].

The reaction was stopped by boiling the samples at 100° C. for 10 minutes, followed by centrifugation at 780×g at 4° C. for 10 minutes. Values obtained represent the average of LAPase activity determined in triplicate.

TABLE 2

Summary of Purification of LAP from Human Breast Carcinoma Parental Cells

| Step | Protein[1] (mg) | Total Activity[2] (nmole/min) | Specific Activity[2] (nmole/min/mg) | Fold | Yield % |
|---|---|---|---|---|---|
| Supernatant | 15.4 | 98.21 | 6.37 | 1 | 100 |
| Gel Permeation | 4.2 | 82.13 | 19.55 | 3.07 | 83.63 |
| Cellulose DEAE | 0.72 | 48.25 | 67.01 | 10.51 | 49.13 |
| Bestatin-Sepharose | 0.005 | 37.11 | 7422 | 1165 | 37.79 |

[1] the amount of protein was determined after alkaline hydrolysis and quantitative ninhydrin detection of hydrolyzed material as described by Pulido-Cejudo et al. [J. Chromatogr. B 660 (1994) 37–47)].
[2] determined fluorometrically using leucine-β-naphtylamide as a subtrate as described by [Kuramochi, H., et al. (1987) J. Antibiot. , 40,1605–1611].

Example 3

Monoclonal Antibody Production and Purification

In producing the hybridoma cell line 7B6 secreting the mouse monoclonal antibody to 17-β-Estradiol-stimulated LAPase, protocols for antigen preparation for immunization, preparation of spleen cells from immune animals, fusion of spleen cells with myeloma cells and plating of fused cells in selective medium was conducted following detailed guidelines described by Campbell [Burdon RH, Knippenberg PHV (eds): Laboratory Techniques in Biochemistry and Molecular Biology, Amsterdam, Elsevier, p219 (1984)] and by Lietzke and Unsicker [Leitzke R. Unsicker K: A Statistical Approach to Determine Monoclonality After Limiting Cell Plating of a Hybridoma Clone, J Immunol Methods 76:223 (1985)].

Briefly, the primary immunization was performed with purified es-LAPase following desalting. Boosts with purified es-LAPase were performed at days 14, 35 & 56. BALB/c mice were screened at days 24 & 45. The mice were sacrificed at day 59 and the splenocytes from the best responder were fused with myeloma cells. Screening was performed by dot blot immunostaining on nitrocellulose.

The hybridoma clone 7B6 was obtained by single cell cloning using limiting dilution. Four dilution tubes in series containing hybridoma cells with medium supplement with 20% FBS+2X OPI were prepared. 100 μl of each dilution was plated in a 96-well plate with 50 μl of splenocyte feeder cells in each well and placed inside a 37° C. 5% $CO_2$ incubator. At day 7, supernatants from each well were removed and screened by dot blot immunostaining on nitrocellulose.

Hybridoma clone 7B6 cells were transferred from the 96 well plate to 0.5 ml medium supplemented with 20% FBS+ 1X OPI+1X HAT in a 24 well plate. Once the cells were dense, they were transferred into 5 mls in a 60 mm dish and then transferred to 10 mls in a 100 mm dish. Once in the 60 mm dish, the cells were weened off hypoxanthine, thymidine and aminopterin. 7B6 hybridoma cells were continued to be grown until in a log phase of growth. Anti-es-LAPase, Mab 7B6 was isolated from collected hybridoma 7B6 cell supernatant by affinity chromatography using Immunopure IgG as per described by manufacturer. Screening was performed by dot blot immunostaining on nitrocellulose.

The isotype of Mab 7B6 was determined using Sigma's Immunotype Kit. Briefly, the assay involves binding of Mab 7B6 to a precoated isotyping nitrocellulose membrane strip followed by immunodetection using a sensitive biotin-avidin-enzyme detection system. The immunoglobulin isotype is revealed by self description. ELISA analysis of Human Breast Carcinoma parental cell lines was conducted to demonstrate the reactivity of Mab 7B6 against human es-LAPase. Briefly, $50 \times 10^3$ parental cells were plated per well in a 96 well plate in RPMI 1640 medium+10% FCS+ 100 U/ml Penicillin+100 µg/ml Streptomycin. The plated cells were cultivated at 37° C. 5% $CO_2$ for 24 hours. The cell supernatants were removed, the cells were washed with PBS and subsequently fixed with 1% gluteraldehyde in PBS for 1 hour at room temperature. Washing with PBS occurred prior to blocking with casein for 1 hour at 37° C. 5% $CO_2$. Following another wash with PBS, serial dilutions of Mab 7B6 were added to the wells and allowed to incubate for 2 hours at 37° C. 5% $CO_2$. Demonstration of the reactivity of Mab 7B6 was revealed upon the addition of a secondary antibody, anti-(IgG+IgM) peroxidase conjugated goat anti-mouse IgG+IgM (H+L) followed by the substate, OPD.

Following purification of the Mab 7B6, the corresponding IgG1 a isotype was subsequently immobilized to a DSS cross-linking system obtained from Pierce (Rockford, Ill., U.S.A) according to the procedures described by the manufacturer.

Figure 2:
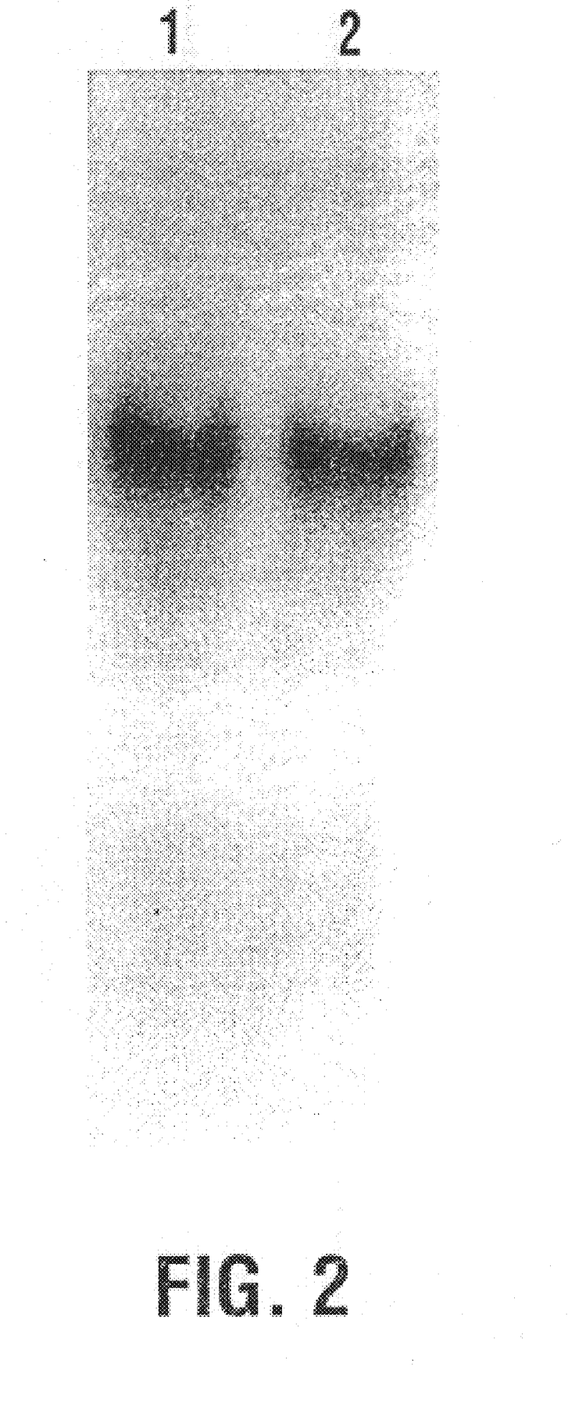
FIG. 2 is a SDS PAGE of crude (lane 1) and purified LAPase (lane 2) followed by western blot with MAb 7B6.

As shown in FIG. 2, Mab 7B6 specifically reacts with es-LAPase in both crude cell supernatants as well as purified es-LAPase after SDS PAGE followed by immunoelectrotransfer. The estimated Molecular Mass of 17-β-Estradiol-stimulated LAPase was 315 kDa as estimated by Gel Permeation on a Bio-Sil SEC-250 column (600×7.5 mm) using Thyroglobulin (MW 670 kDa); Bovine Gamma Globulin (MW 158 kDa); Chiken ovalbumin (MW 44 kDa) and Equine Myoglobin (17 kDa).

Example 4

Effect of Estrogen on Increased Infectivity of HUT78 Cells

Estrogen-mediated HIV-induced cytopathic effect was determined as described by G. Pulido-Cejudo et al. [Pulido-Cejudo, G., Conway, B., Proulx, P., Brown, R., and Izaguirre, C. A. (1997). *Antiviral Research*, 36: 167–177]. The sensitivity of $CD4^+$ T-HUT78 cells to HIV viral infection was determined by measuring the activity of reverse transcriptase in cells infected in the presence/absence of 17-β-Estradiol.

In light of both the clinical observations indicating the hypersensitivity of women to HIV infection [Centers for Disease Control and Prevention. (1996). *HIV/AIDS Surveill. Rep.* 8. Atlanta, Ga., Wortley, P. M., and Flemming, P. L. (1997). *JAMA,* 278: 911–916.] as well as the role of LAPase in viral entry [Pulido-Cejudo, G., Conway, B., Proulx, P., Brown, R., and Izaguirre, C. A. (1997). *Antiviral Research,* 36: 167–177], together with the direct effect of estrogen on LAPase reported supra, the sensitivity of HUT78 cells to HIV viral infection was determined. As shown in Table 3, at 3 days and 5 days post infection, in the presence of estrogen, HIV viral infectivity as determined by the activity of reverse transcriptase (RT) was approximately 4 times higher than control cells infected in the absence of estrogen.

TABLE 3

Effect of Estrogen on increased infectivity

| | RT Activity (cpm × $10^2$/10 µl) | | |
|---|---|---|---|
| | Day 0 (Infection) | Day 3 (Post Infection) | Day 5 (Post Infection) |
| Control | 0.82 | 19.82 | 32.44 |
| Estrogen ($10^{-7}$ M) | 0.68 | 72.42 | 124.44 |

Example 5

Inhibitors of es-LAPase

Human Thioredoxin was purified from $CD_4$+ T MP6 cells as described by Rosen et al. [Rosen, A. et al. (1995) Int. Immunol. 7, 625–633] and compared to purified Thioredoxin activity from *E. Coli.* purchased from SIGMA-ALDRICH Canada (Oakville, Ontario Canada).

Thioredoxin was covalently linked through an amide bond to Ultralink EDC/DADPA bonding matrix (Pierce, Rockford, Ill. U.S.A.) by reacting 5 mg of purified Thioredoxin with the carbodiimide EDC/DADPA matrix following the procedure provided by the manufacturer.

Measurements of LAPase were performed spectrophotometrically at 330 nm to measure product formation of β-naphthylamine, using 182 µM 1-leucine-β-naphthylamide as the substrate. The kinetic assays were performed using a Spectronic Genesys 5 spectrophotometer from Milton Roy (Rochester, N.Y.). Absorbance was recorded every sixty seconds, over a period of 30 min. Enzyme kinetic assays were performed using $8.0 \times 10^{-2}$ U of es-LAPase in a final reaction volume of 600 µl and triplicate samples. The reaction mixture contained the following materials added in order and all kept on ice prior to use: es-LAPase, Calcium-free Hank's solution making up a 600 µl final reaction volume and 182 µM 1-leucine-β-naphthylamide. A corresponding blank without es-LAPase was used as baseline. Both of the cuvettes were transferred to the spectrophotometer where the 1-leucine-β-naphthylamide solution was added last, marking time zero of the reaction. The inhibition studies were carried out in the presence of 167 µM Bestatin, 167 µM reduced Gluthathione and 17 µM reduced thioredoxin.

Figure 3:
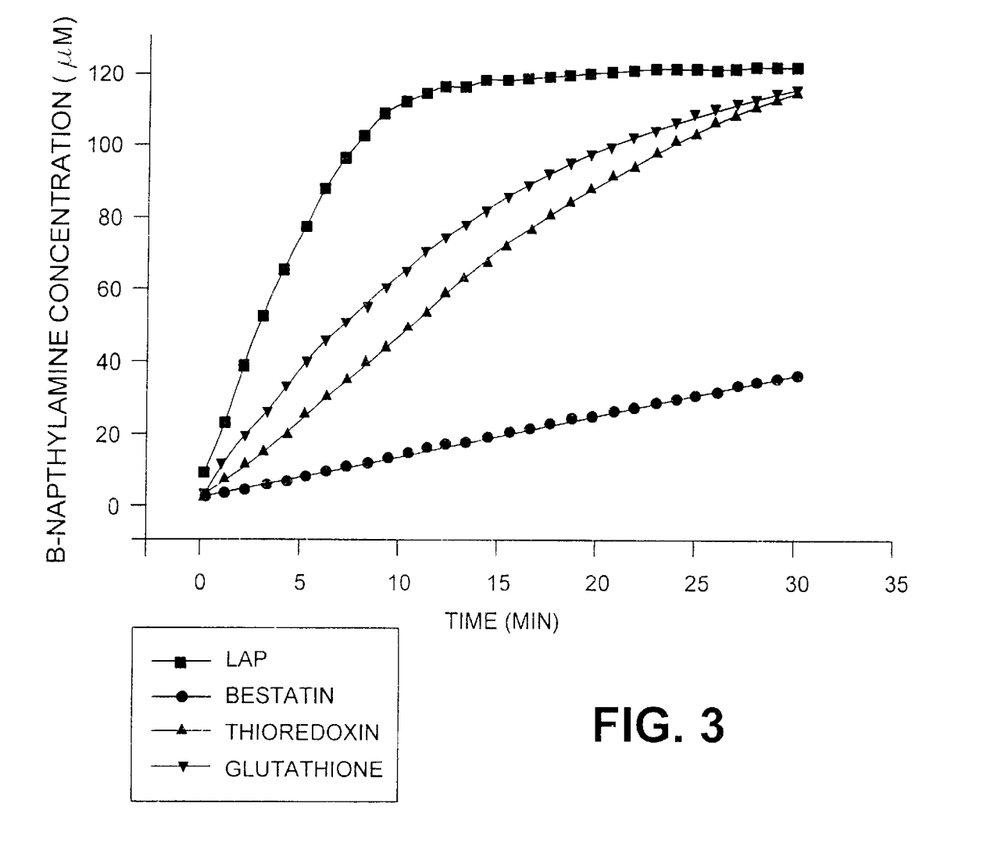
FIG. 3 shows the kinetics of inhibition of LAPase by Bestatin, thioredoxin and glutathione.

FIG. 3 shows the inhibitory effect of both Bestatin and two thiol-containing peptides, reduced thioredoxin and reduced glutathione respectively. Es-LAPase showed significant slower rates of reaction both in the presence of thioredoxin and glutathione in comparison to that observed in the control es-LAPase. In addition, es-LAPase reaction rates were slower in the presence of 17 µM thioredoxin when compared to those observed in samples incubated with 167 µM reduced Gluthathione. In addition, 167 µM Bestatin clearly inhibits es-LAPase activity. As shown in Table 4, reduced thioredoxin is an effective inhibitor of es-LAPase activity. The analysis of the maximum reaction rates (Vmax), Michaelis-Menten (Km) constants and the inhibition constants (Ki) for each inhibitor as presented in Table 4 reveals significant differences in the inhibitory properties of each peptide. In this regard, es-LAPase incubated with Bestatin shows a Vmax value very similar to that observed to es-LAPase alone and a significantly higher Km value. This data confirms the competitive nature of es-LAPase inhibition by Bestatin. In contrast, es-LAPase incubated with reduced thioredoxin leads to a significantly lower Vmax and Km with an intermediate Ki value when compared to those obtained for Bestatin and glutathione. Collectively these data strongly suggest that reduce thioredoxin inhibits es-LAPase in an uncompetitive fashion while with reduced glutahthione es-LAPase inhibition is noncompetitive.

TABLE 4

Bestatin, reduced thioredoxin and glutathione es-LAPase inhibition Constants

| | Vmax ($10^{-6}$ M/min) | Km ($10^{-4}$ M) | Ki ($10^{-6}$ M) |
|---|---|---|---|
| LAPase alone | 36.8 ± 1.9 | 1.67 ± 0.14 | N/A |
| Bestatin 167 $\mu$M | 34.0 ± 3.9 | 48.7 ± 8.4 | 6.22 ± 1.61 |
| Thioredoxin 17 $\mu$M | 5.31 ± 0.02 | 0.234 ± 0.006 | 3.40 ± 0.58 |
| Glutathione 167 $\mu$M | 17.2 ± 1.5 | 1.78 ± 0.25 | 1.53 ± 0.40 |

Example 6

Inhibition of HIV

Twelve hours prior to infection with $HTLV_{IIIb}$, HUT78 cells were incubated in viral culture medium alone or in the presence of Anti-es-LAPase; thioredoxin; Bestatin and Anti-estrogens according to the combinations described below. In the continued presence of each of the factors aforementioned, the cells were subsequently infected at a multiplicity of two infective viral particles per cell for two hours at 25° C. with constant agitation in a final volume of 1.0 ml. Cells were subsequently washed with saline phosphate buffer solution (PBS) and seeded at a density of $1.0 \times 10^5$ cells/ml in RPMI 1640, supplemented with 10% FBS, 100 U/ml penicillin, 100 mg/ml streptomycin in 96-well plates. Syncytium formation was evaluated by light microscopy on days 3, 5 and 7. At appropriate time points, the cells in selected wells were subjected to psoralen/ultraviolet light inactivation (Watson et al., 1990) air-dried and fixed on glass plates with cold acetone. Indirect immunofluorescent staining was performed using a modification of standard procedures (Aldovini, A. and Walker, B. D. (1990) Techniques in HIV Research. Stockton Press, New York; Johnson, G. D. and Nogueira Araujo, G. M.(1981) J. Immunol. Methods , 43, 349–350. Plates were incubated for 10 minutes in blocking buffer (PBS, 5% goat serum) and reacted with either control mouse serum or anti-HIV-1 gag (p24, p55) monoclonal antibodies (Olympus Inmunochemicals), which were diluted 1:100 in blocking buffer, for 30 minutes at room temperature. Cells were washed three times with PBS and incubated for 30 minutes with goat anti-mouse-FITC antibodies (Beckton and Dickinson). Slides were mounted in paraphenylenediamine/glycerol [Johnson, G. D. and Nogueira Araujo, G. M.(1981) J. Immunol. Methods , 43, 349–350] and fluorescent cells were counted.

Following HIV-1 infection of HUT-78 cells, the proviral load in each experimental condition was determined by PCR [Conway, B., Shui-Wah Ko, D. and Cameron, W. (1995) Clin. Diag. Virol. 3, 95–104].

Prior to infection, HUT78 cells were washed three times with PBS and the cell viability was determined. Infection was performed as described above. At indicated time intervals, 1.0 mil aliquots of were taken and p24 antigen quantified using a commercial ELISA kit (p24 Antigen Capture ELISA, ABBOTT Diagnostics Division), following the instructions of the manufacturer.

The Effect of Mab 7B6, thioredoxin, Bestatin and antiestrogens on the viability of HUT78 cells was assessed as follows. HUT78 cells were seeded at a density of $1.0 \times 10^5$ cells/ml in RPMI 1640, 10% FBS, 100 U/ml penicillin, 100 mg/mil streptomycin in the presence or absence of each of the compounds aforementioned. The medium was changed every third day and cell viability was determined by trypan blue dye exclusion. Thymidine incorporation was also measured [Noma, T., Klein, B., Cupissol, D., Yata, J. and Serrou, B.(1984). Int. J. Immunopharmac., 6, 87–92.] in duplicate cultures on day 7. Values obtained represent the mean±s.d. (n=10).

Incubation of HUT 78 cells with Mab 7B6-Protein G Matrices 7 hours prior to Infection with HIV-1 significantly reduces the number of HIV-1 proviral copies when compared to control cells pre-incubated with mouse IgG1-Protein G matrices (see Table 5).

TABLE 5

Inhibition of HIV-1 proviral copies by Anti-es-LAPase Mab 7B6 bound to Protein G.

| | Days Post-infection | | | |
|---|---|---|---|---|
| | 0 | 3 | 5 | 7 |
| Mab 7B6 (100 ng/1 ml) | 0 | 86 ± 5 | 189 ± 2 | 220 ± 24 |
| Control IgGla (100 ng/1 ml) | 0 | 2014 ± 89 | 4002 ± 46 | 5551 ± 92 |

Incubation of HUT 78 cells with thioredoxin-EDC/DADPA Matrices 7 hours prior to Infection with HIV-1 significantly reduces the number of HIV-1 proviral copies when compared to control cells pre-incubated with control myoglobin IgG1-Protein G matrices (see Table 6).

TABLE 6

Inhibition of HIV-1 Proviral copies by thioredoxin-EDC/DADPA Matrix compared to Bestatin-HIV inhibition

| | Days Post-infection | | | |
|---|---|---|---|---|
| | 0 | 3 | 5 | 7 |
| Thioredoxin (40 ng/5 ml) | 0 | 4 ± 1 | 12 ± 3 | 122 ± 8 |
| Bestatin (120 $\mu$g/ml | 0 | 7 ± 2 | 29 ± 3 | 457 ± 12 |
| Control/Myoglobin (40 ng/5 ml) | 0 | 2414 ± 178 | 4122 ± 121 | 5851 ± 123 |

The independent inhibition mediated by thioredoxin and anti-LAPase 7B6 monoclonal antibodies can be synergized by their simultaneous addition to HUT-78 cells prior to HIV-1 infection (Table 7). In this context, without wishing to be bound by any theory, the synergistic effect of thioredoxin and of non-inhibitory LAPase 7B6 monoclonal antibodies imply that both LAPase activity and Viral-protein interactions may be required during HIV-1 infectivity. It equally suggests that the elevation of plasma thioredoxin levels detected in late stages of HIV infection as reported by Nakamura et al. (1996, Int. Immunol. 8, 603–611) may not only compensate for intracellular glutathione depletion but it may also be directly implicated in reducing HIV viral load.

TABLE 7

Synergistic Inhibition of HIV-1 Proviral copies by
thioredoxin-EDC/DADPA and Anti-LAPase 7B6 combined Matrices

| | Days Post-infection | | | |
|---|---|---|---|---|
| | 0 | 3 | 5 | 7 |
| Mab 7B6/Thioredoxin (100 ng/40 ng/10 ml) | 0 | 12 ± 3 | 69 ± 5 | 88 ± 12 |
| Control IgG1a/Myoglobin (100 ng/40 ml) | 0 | 1914 ± 55 | 4330 ± 26 | 5110 ± 12 |

As shown in Example 4, exposure to 17-β-estradiol increased LAPase activity, which in turn resulted in an increase in HIV infectivity. Thus, the selective increase in HIV infectivity of women between 1991–1995 regardless of race or mode of exposure to HIV virus could be explained in terms of the effect of estrogen on LAPase.

These observations, together with the uncompetitive inhibitory effect of thioredoxin on LAPase raise the possibility of the use of combined therapy for the prevention and treatment of AIDS.

The combined anti-HIV effect of LAPase inhibition by Mab 7B6, thioredoxin and Bestatin together with the administration of anti-estrogens to hamper the effect of estrogen on LAPase activity and hence of HIV infection can lead to a promising therapy against AIDS. Therefore, Tamoxifen, Droloxifene, Raloxifene, Idoxifene, 4-hydroxyandrostenedione and the 3β,5α-tetrahydro derivative of Norethisterone, which are all anti-estrogen compounds, were tested for their ability to senergize the antiviral properties of thioredoxin, Bestatin and of Mab 7B6.

Based on the effect of anti-estrogens on the antiviral properties of combined MAb 7B6/thioredoxin matrices, the most effective combination for the complete in vitro inhibition of HIV-1 infection was evaluated according to the overall effect on the reduction of cytopathicity, p24 levels and proviral load. For simplicity in these experiments determinations on the various parameters herein above aforementioned were determined on day 5 post-infection. Prior to infection cells were simultaneously incubated with thioredoxin-EDC/DADPA and Anti-es-LAPase 7B6 Matrices. The inhibitory effect of this anti-estrogens is summarized in Table 8. All anti-estrogenic compounds were used at a final concentration of $10^{-7}$M.

TABLE 8

Combined antiviral effect of Mab 7B6 and thioredoxin matrices in
combination with anti-estrogens
Day 5 Post-infection

| Agent | P24 (nmoles/ml) | Cytopathicity (Syncytia/well) | Proviral Load (copies) |
|---|---|---|---|
| Control (No additions) | 1.82 ± .003 | 117 ± 6 | 3777 ± 82 |
| 4-hydroxyandrostenedione | 0.02 ± .001 | 4.0 ± 0.4 | 12 |
| Raloxifene | 0.01 ± .002 | 3.3 ± 0.1 | 8 |
| 3β,5α-tetrahydro Norethisterone | 0 | 0 | 2 |
| Tamoxifen, | 0 | 0 | 0 |
| Droloxifene, | 0.04 ± .003 | 5.2 ± 0.6 | 14 |
| Idoxifene, | 0 | 0 | 0 |

All cited references and patents or patent applications are incorporated herein by reference.

The present invention has been defined in terms of certain examples, which are not to be construed as limiting. The full scope of the present invention is defined in the following claims.

The embodiments of the invention in which an exclusive property of privilege is claimed are defined as follows:

1. A method for reducing the susceptibility of T lymphocytes to HIV infection comprising contacting said T lymphocytes with a sufficient amount of an uncompetitive inhibitor of estrogen-stimulated leucine aminopeptidase (es-LAPase).

2. The method according to claim 1 wherein the uncompetitive inhibitor is a thiol containing compound.

3. The method according to claim 2 wherein the thiol containing compound is thioredoxin.

4. A method for reducing the susceptibility of T lymphocytes to HIV infection comprising contacting said T lymphocytes with a sufficient amount of an antibody specific for es-LAPase.

5. The method according to claim 4 wherein the antibody is a monoclonal antibody.

6. The method according to claim 5 wherein the monoclonal antibody is produced by hybridoma cell line 7B6 (International Depositary Authority of Canada # IDAC 230300-1, Mar. 23, 2000).

7. A method according to claim 4, wherein the method further comprises contacting said T lymphocytes with at least one LAPase inhibitor.

8. The method according to claim 7 wherein the inhibitor is selected from the group consisting of Bestatin and a thiol containing compound.

9. The method according to claim 8 wherein the thiol containing compound is selected from the group consisting of thioredoxin and glutathione.

10. The method according to claim 9 wherein the antibody is a monoclonal antibody.

11. The method according to claim 10 wherein the monoclonal antibody is produced by hybridoma cell line 7B6 (International Depositary Authority of Canada # IDAC 230300-1, Mar. 23, 2000).

12. A method according to claim 7, wherein the method further comprises contacting said T lymphocytes with at least one anti-estrogen compound.

13. The method according to claim 12 wherein the anti-estrogen is selected from the group consisting of 4-hydroxyandrostenedione, Raloxifene, 3β,5α-tetrahydro Norethisterone, Tamoxifen, Droloxifene, Idoxifene.

14. A method for reducing the susceptibility of T lymphocytes to HIV infection comprising administering to a patient in need thereof, a pharmaceutically effective amount of a composition which comprises an antibody specific to es-LAPase and a pharmaceutically acceptable carrier.

15. The method according to claim 14 wherein the antibody is a monoclonal antibody.

16. The method according to claim 15 wherein the monoclonal antibody is produced by hybridoma cell line 7B6 (International Depositary Authority of Canada # IDAC 230300-1, Mar. 23, 2000).

17. A method for reducing the susceptibility of T lymphocytes to HIV infection comprising administering to a patient in need thereof, a pharmaceutically effective amount of a composition which comprises an uncompetitive inhibitor of estrogen-stimulated LAPase and a pharmaceutically acceptable carrier.

18. The method according to claim 17 wherein the uncompetitive inhibitor is a thiol containing compound.

19. The method according to claim 18 wherein the thiol containing compound is thioredoxin.

20. The method according to claim 14 wherein the composition further comprises an uncompetitive inhibitor of LAPase.

21. The method according to claim 20 wherein the antibody is a monoclonal antibody.

22. The method according to claim 21 wherein the monoclonal antibody is produced by hybridoma cell line 7B6 (International Depositary Authority of Canada # IDAC 230300-1, Mar. 23, 2000).

23. The method according to claim 22 wherein the uncompetitive inhibitor is a thiol containing compound.

24. The method according to claim 23 wherein the thiol containing compound is thioredoxin.

25. The method according to claim 20 wherein the composition further comprises an anti-estrogen compound.

26. The method according to claim 25 wherein the anti-estrogen is selected from the group consisting of 4-hydroxyandrostenedione, Raloxifene, 3β,5α-tetrahydro Norethisterone, Tamoxifen, Droloxifene, Idoxifene.

27. A composition comprising an antibody specific to es-LAPase and an inhibitor of LAPase.

28. The composition according to claim 27 wherein the antibody is a monoclonal antibody.

29. The composition according to claim 28 wherein the monoclonal antibody is produced by hybridoma cell line 7B6 (International Depositary Authority of Canada # IDAC 230300-1, Mar. 23, 2000).

30. The composition according to claim 27 wherein the inhibitor is selected from the group consisting of Bestatin and a thiol containing compound.

31. The composition according to claim 30 wherein the thiol containing compound is selected from the group consisting of thioredoxin and glutathione.

32. The composition according to claim 27 wherein the composition further comprises an anti-estrogen compound.

33. The composition according to claim 32 wherein the anti-estrogen is selected from the group consisting of 4-hydroxyandrostenedione, Raloxifene, 3β,5α-tetrahydro Norethisterone, Tamoxifen, Droloxifene, Idoxifene.

34. A method for reducing the susceptibility of T lymphocytes to HIV infection comprising contacting said T lymphocytes with a sufficient amount of: an uncompetitive inhibitor of LAPase, a monoclonal antibody specific for es-LAPase and an anti-estrogen.

35. A method for reducing the susceptibility of T lymphocytes to HIV infection comprising contacting said T lymphocytes with a sufficient amount of: an uncompetitive inhibitor of LAPase, a competitive inhibitor of LAPase, a monoclonal antibody specific for es-LAPase and an anti-estrogen.

* * * * *